(12) United States Patent
Bril et al.

(10) Patent No.: US 12,325,738 B2
(45) Date of Patent: Jun. 10, 2025

(54) TREATMENT OF CIDP

(71) Applicant: CSL Behring AG, Bern (CH)

(72) Inventors: Vera Bril, Toronto (CA); John-Philip Lawo, Schwanewede (DE)

(73) Assignee: CSL BEHRING AG, Bern (CH)

( * ) Notice: Subject to any disclaimer, the term of this patent is extended or adjusted under 35 U.S.C. 154(b) by 1098 days.

(21) Appl. No.: 17/056,632

(22) PCT Filed: May 23, 2019

(86) PCT No.: PCT/EP2019/063322
§ 371 (c)(1),
(2) Date: Nov. 18, 2020

(87) PCT Pub. No.: WO2019/224304
PCT Pub. Date: Nov. 28, 2019

(65) Prior Publication Data
US 2021/0206837 A1 Jul. 8, 2021

(30) Foreign Application Priority Data
May 23, 2018 (EP) .................................. 18173860

(51) Int. Cl.
| | |
|---|---|
| C07K 16/06 | (2006.01) |
| A61B 5/00 | (2006.01) |
| A61B 5/388 | (2021.01) |
| A61B 5/389 | (2021.01) |
| A61P 25/02 | (2006.01) |

(52) U.S. Cl.
CPC .............. *C07K 16/06* (2013.01); *A61B 5/388* (2021.01); *A61B 5/389* (2021.01); *A61B 5/4082* (2013.01); *A61B 5/6824* (2013.01); *A61B 5/6829* (2013.01); *A61P 25/02* (2018.01)

(58) Field of Classification Search
None
See application file for complete search history.

(56) References Cited

PUBLICATIONS

Grüter et al., Axonal damage determines clinical disability in chronic inflammatory demyelinating polyradiculoneuropathy (CIDP) A prospective cohort study of different CIDP subtypes and disease stages. Eur J Neurol. 29:583-592, 2022.*
Schaik et al., Subcutaneous immunoglobulin for maintenance treatment in chronic inflammatory demyelinating polyneuropathy (The PATH Study): study protocol for a randomized controlled trial. Trials 17:345, pp. 1-15, 2016.*
Bolton, C.F. et al., "Minimum Standards for Electromyography in Canada: a Statement of the Canadian Society of Clinical Neurophysiologists," The Canadian Journalof Neurological Sciences, vol. 27, No. 4, pp. 288-291 (2000).
Hughes, Richard, M.D., et al. "Randomized Controlled Trial of Intravenous Immunoglobulin Versus Oral Prednisolone in Chronic Inflammatory Demyelinating Polyradiculoneuropathy," Annals of Neurology, vol. 50, No. 2 pp. 195-201 (2001).
Léger, Jean-Marc et al., "Intravenous Immunoglobulin Therapy in Multifocal Motor Neuropathy a Double-Blind, Placebo-Controlled Study," Brain, vol. 124, No. 1, pp. 145-153 (2001).
Bril, Vera, M.D. et al., "Validation of the Toronto Clinical Scoring System for Diabetic Polyneuropathy," Diabetes Care, vol. 25, No. 11, pp. 2048-2052 (2002).
Cocito, Dario et al., "Intravenous immunoglobulin as first treatment in diabetics with concomitant distal symmetric axonal polyneuropathy and CIDP," Journal of Neurology, vol. 249, No. 6, pp. 719-722, Medline Abstract (2002).
Köller, Hubertus, M.D., et al., "Chronic Inflammatory Demyelinating Polyneuropathy," The New England Journal of Medicine, vol. 352, No. 13, pp. 1343-1356 (2005).
Hughes, Richard A.C. et al., "Intravenous immune globulin (10% caprylate-chromatography purified) for the treatment of chronic inflammatory demyelinating polyradiculoneuropathy (ICE study): a randomised placebo-controlled trial." The Lancet, Neurology, vol. 7, No. 2, pp. 136-144 (2008).
Hughes, Richard A. C., "Intravenous immunoglobulin for chronic inflammatory demyelinating polyradiculoneuropathy: the ICE trial," Expert Review of Neurotherapeutics, vol. 9, No. 6, pp. 789-795 (2009).
Joint Task Force of the EFNS and the PNS, "European Federation of Neurological Societies/Peripheral Nerve Society Guideline on management of chronic inflammatory demyelinating polyradiculoneuropathy: Report of a joint task force of the European Federation of Neurological Societies and the Peripheral Nerve Society—First Revision," Journal of the Peripheral Nervous System, vol. 15, pp. 1-9 (2010).
Van Nes, S.I. et al. "Rasch-built Overall Disability Scale (R-ODS) for immune-mediated peripheral neuropathies," Neurology, vol. 76, No. 4, pp. 337-345 (2011).
Dunnigan, Samantha K. et al., "Comparison of diabetes patients with "demyelinating" diabetic sensorimotor polyneuropathy to those diagnosed with CIDP," Brain and Behavior, vol. 3, No. 6, pp. 656-663 (2013).
Dunnigan, Samantha K. et al., "Conduction Slowing in Diabetic Sensorimotor Polyneuropathy," Diabetes Care, vol. 36, pp. 3684-3690 (2013).
Dunnigan, Samantha K. et al., "The Characteristics of Chronic Inflammatory Demyelinating Polyneuropathy in Patients with and without Diabetes—an Observational Study," PLOS ONE, vol. 9, No. 2, pp. 1-6 (2014).
Bril, Vera M.D., et al., "ORBCoN Spring Symposium," pp. 1-73 (2015).
Mathey, Emily K. et al., "Chronic inflammatory demyelinating polyradiculoneuropathy: from pathology to phenotype," Journal Neurology, Neurosurgery, and Psychiatry, vol. 86, No. 9, pp. 973-985 (2015).

(Continued)

*Primary Examiner* — Ruixiang Li
(74) *Attorney, Agent, or Firm* — Finnegan, Henderson, Farabow, Garrett & Dunner LLP

(57) ABSTRACT

The present invention relates to an immunoglobulin therapy. In particular, an immunoglobulin therapy for treating CIDP with non-axonal damage or mild axonal damage is provided.

10 Claims, 5 Drawing Sheets

(56) References Cited

PUBLICATIONS

Bril, V. et al., "Axonal function predicts response to subcutaneous immunoglobulin in chronic inflammatory demyelinating polyneuropathy: The PATH study," European Journal of Neurology, Supplement 2, vol. 25, EMBASE-Abstract (2018).

Bril, V. et al., "Axonal function predicts response to subcutaneous immunoglobulin in CIDP: The path study," Journal of Neuromuscular Diseases vol. 5, Supplement 1, EMBASE-Abstract (2018).

Van Schaik, Ivo N. et al., "Subcutaneous immunoglobulin for maintenance treatment in chronic inflammatory demyelinating polyneuropathy (PATH): a randomised, double-blind, placebo-controlled, phase 3 trial," The Lancet. Neurology, vol. 17, No. 1, pp. 35-46 (2018).

International Search Report for International Application No. PCT/EP2019/063322, dated Jul. 16, 2019.

Written Opinion of the International Searching Authority for International Application No. PCT/EP2019/063322, dated Jul. 16, 2019.

\* cited by examiner

TREATMENT OF CIDP

This application is the United States national stage entry under 35 U.S.C. § 371 of International Application No. PCT/EP2019/063322, filed on May 23, 2019, which claims priority to European Patent Application No. 18173860.0, filed on May 23, 2018. The contents of these applications are each incorporated herein by reference in their entirety.

FIELD OF THE INVENTION

The present invention relates to immunoglobulin products for use in the treatment of chronic inflammatory demyelinating polyneuropathy. The provided treatment is particularly efficacious in patients suffering for CIDP with non-axonal damage or mild axonal damage.

BACKGROUND

Chronic inflammatory demyelinating polyneuropathy (CIDP) is an autoimmune disease that targets myelin sheaths, specifically in the peripheral nerves, and causes progressive weakness and sensory loss. Swelling of nerve roots is also a characteristic of the disease. Although it can occur at any age and in both genders, CIDP is more common in young adults, and it is more common in men than women.

CIDP causes peripheral neuropathy, which is manifest by sensory loss, weakness, or pain, alone or in combination, in the arms, legs, or other parts of the body. It can cause a symmetric or multifocal neuropathy and affect the proximal or distal muscles. CIDP may be associated with certain other diseases. For example, it has been found that CIDP is diagnosed in one third of human immunodeficiency virus (HIV)-seropositive patients referred for peripheral nerve diseases. CIDP also occurs in subjects afflicted with lupus, paraproteinemia, lymphoma or diabetes. The course of CIDP may vary widely among individuals. Some patients may have a bout of CIDP followed by spontaneous recovery, while other patients may have many bouts with only partial recovery in between relapses.

CIDP is diagnosed based on the clinical presentation, evidence for demyelination on electrodiagnostic studies or pathological studies of biopsied nerves, and elimination of other known causes of neuropathy such as genetic defects, osteosclerotic myeloma or IgM monoclonal gammopathy.

Untreated, CIDP is characterized by accumulating disability that requires physical and occupational therapy, orthotic devices and long-term treatment. Early intervention can prevent permanent damage and disability. Current methods of treatment for CIDP include administration of corticosteroids, such as prednisone, which may be prescribed alone or in combination with immunosuppressant drugs. Immunosuppressant drugs may also be given in the absence of a steroid. Individually adjusted intravenous immunoglobulin (IVIG) therapy is also effective and is currently being used for treating CIDP.

SUMMARY OF THE INVENTION

The present invention is based on the unexpected and surprising finding that immunoglobulin therapy is particularly beneficial for patients suffering from CIDP who do not exhibit axonal damage. Further, this treatment is beneficial for patients suffering from mild axonal damage.

The present invention provides an immunoglobulin product for use in a method of treating chronic inflammatory demyelinating polyneuropathy (CIDP), wherein the method comprises selecting a patient who has non-axonal damage for treatment with the immunoglobulin product. The present invention also provides an immunoglobulin product for use in a method of treating chronic inflammatory demyelinating polyneuropathy (CIDP), wherein the method comprises selecting a patient who has mild axonal damage for treatment with the immunoglobulin product.

In one embodiment, the selection of a patient with non-axonal damage or mild axonal damage involves an electrophysiology measurement. The electrophysiology measurement may involve the steps of
  (i) supramaximal nerve stimulation using a stimulation electrode, and
  (ii) recording the amplitude of the compound muscle action potential using a recording electrode.

According to one embodiment, the selection may be based on a pre-determined cut-off amplitude for the compound muscle action potential. In one embodiment, the electrophysiology measurements are carried out at the wrist. In one embodiment, the electrophysiology measurements are carried out at the foot. In one embodiment, the pre-determined cut-off amplitude for the wrist is >2 mV. In one embodiment, the pre-determined cut-off amplitude for the foot is >1 mV. In one embodiment, the pre-determined cut-off amplitude is at least 50% of the mean amplitude measured in a healthy subject. Nerves that can be measured include the ulnar motor nerve, the median motor nerve, and/or the peroneal motor nerve. Alternatively, non-axonal damage or mild axonal damage may be determined by nerve biopsy.

Figure 1:
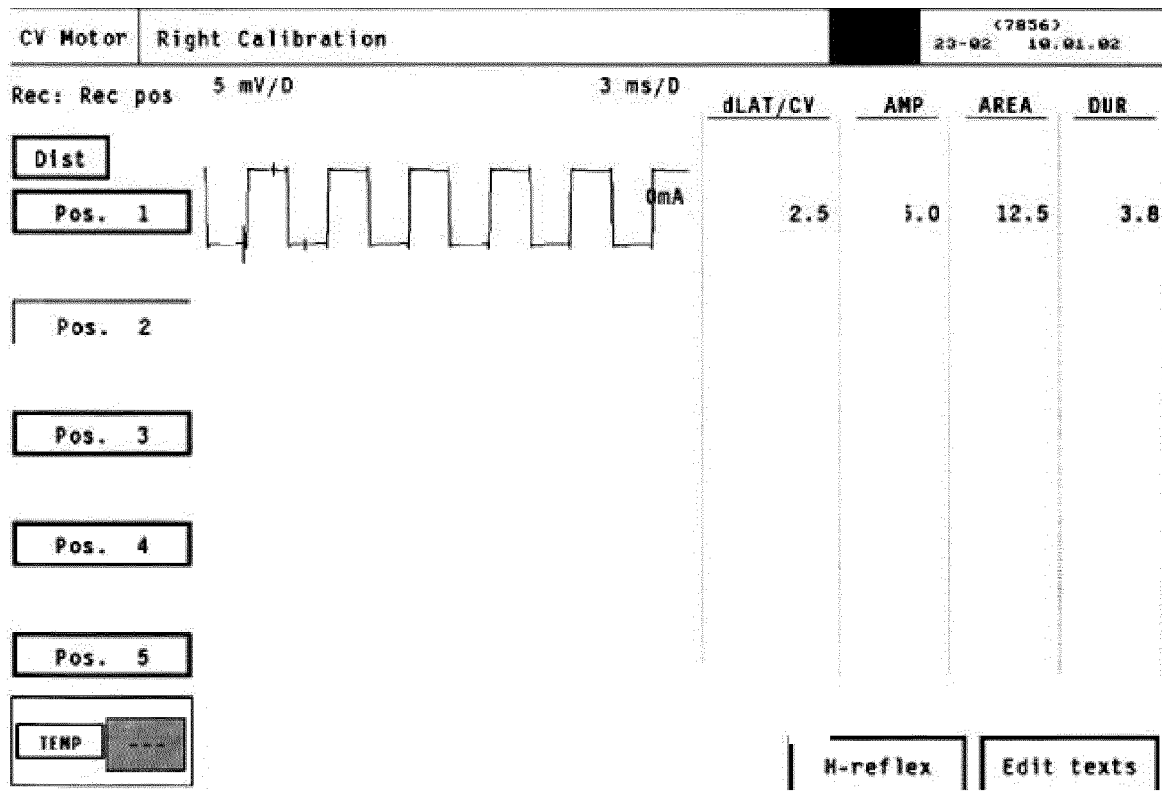
FIG. 1: Example of a Motor Calibration Signal Recording.

S2: Below Fibular Head; S3: Lateral Popliteal Fossa. Temperature probe placed in lower leg.

DETAILED DESCRIPTION

Chronic Inflammatory Demyelinating Polyneuropathy (CIDP)

CIDP is an acquired polyneuropathy within the peripheral nerve system with an assumed autoimmune-mediated pathogenesis. CIDP is characterized by symmetrical weakness in both proximal and distal muscles that worsens progressively. The condition is usually, but not always, associated with impaired sensation, absent or diminished tendon reflexes, an elevated cerebrospinal fluid protein level, and changes in electrophysiology parameters. Nerve biopsy specimens are characterized by signs of demyelination. The clinical course can be relapsing or chronic and progressive (see, e.g., Mathey E K, et al. J Neurol Neurosurg Psychiatry 2015; 86:973-985; Köller H, et al. N Engl J Med. 2005; 352(13): 1343-1356), the former being much more common in young adults. CIDP is a rare disease with an estimated prevalence of about 1.6 to 8.9 per 100,000 adults and about 0.5 per 100,000 children. CIDP may be diagnosed as described by the Joint Task Force of the EFNS and the PNS (Journal of the Peripheral Nervous System 15:1-9 (2010)).

The following conditions are identical or considered essentially identical to CIDP and are thus encompassed by the claims: "chronic relapsing polyneuropathy", "chronic idiopathic demyelinating polyneuropathy", "chronic inflammatory demyelinating polyradiculoneuropathy", and "chronic acquired demyelinating polyneuropathy" ("CADP").

CIDP patients may be classified into certain groups depending on electrophysiology parameters. Such electrophysiology parameters may be determined by analyzing a combination of nerve conduction parameters including latency, conduction velocity and amplitude parameters. These parameters may be measured at distal sites. Standard nerve conduction studies may be performed on the wrist, above the elbow, at the elbow, at the ankle, below the fibular head, at the lateral popliteal fossa. Nerves measured may be readily accessible nerves such as median motor and sensory nerves, ulnar motor nerves, peroneal motor nerves, and sural sensory nerves (in particular, the ulnar motor nerve (N. ulnaris), the median motor nerve (N. medianus) or the peroneal motor nerve (N. peronaeus)) by using the Counterpoint instrument (Medtronic, Mississauga, Canada) or a comparable electromyography device.

Recordings may be performed with temperature control (32-34° C.), careful distance measurements, and recording of well-defined and artifact-free responses. Conventional nerve conduction studies are performed using surface stimulating and recording techniques. The amplitudes of the motor responses, or compound muscle action potentials (CMAP), are measured from baseline to negative peak and the size of the distal response (obtained, for example, in the hand or foot) depends on the number of surviving nerve fibers or axons. When the CMAP amplitude is reduced to certain levels, then the nerve is considered to have lost many axons and the damage is thought to be primarily "axonal". Alternatively, if the distal CMAP amplitude is preserved, then the damage is thought to be more demyelinating in nature.

In one embodiment, the amplitude of the compound muscle action potential is measured upon supramaximal stimulation. The measurement may be carried out, for example, at the wrist or at the foot. In a preferred embodiment, the measurement is carried out at the foot.

The electrophysiology measurement may be carried out at the ulnar motor nerve (N. ulnaris), the median motor nerve (N. medianus) or the peroneal motor nerve (N. peronaeus).

A CIDP patient may be identified as having non-axonal damage or mild axonal damage when exhibiting an amplitude of >1 mV at the foot. Also, a CIDP patient may be identified as having non-axonal damage or mild axonal damage when exhibiting an amplitude of >2 mV at the wrist. In another embodiment, a CIDP patient may be identified as having non-axonal damage or mild axonal damage when exhibiting an amplitude that is at least 50% of the mean amplitude measured in a healthy subject.

The electrophysiology parameters are not only dependent on the CIDP status of a patient, but they may also depend on other factors such as the age of the patient.

CIDP may occur with axonal damage or without axonal damage (non-axonal damage). In CIDP with axonal damage, axons are degenerated. Axonal damage can be further defined as mild axonal damage or as severe axonal damage. In CIDP with non-axonal damage, axon myelination is damaged.

Patients may be classified as suffering from CIDP with axonal damage (mild or severe) or CIDP with non-axonal damage. Certain electrophysiology parameters may be an indication for axonal damage (mild or severe) or non-axonal damage. Accordingly, CIDP patients exhibiting such electrophysiology parameters may categorized as patients with assumed non-axonal damage or assumed axonal damage. Electrophysiology parameters may be determined by analyzing a combination of nerve conduction parameters including latency, conduction velocity and amplitude parameters as described above.

For example, CIDP patients exhibiting an amplitude of >1 mV for the foot, and/or >2 mV for the wrist can be considered as patients with non-axonal damage or mild axonal damage.

Alternatively or in addition, patients may be classified as suffering from CIDP with axonal damage or CIDP with non-axonal damage by taking and analyzing nerve biopsies. For example, full-thickness sural nerve biopsies may be performed at an anatomical location posterior to the lateral malleolus by an experienced and protocol-trained surgeon. The biopsies may be done using local anesthetic (1% lidocaine without epinephrine). A 7 cm segment of nerve may be obtained with care to avoid tension on the nerve, then sectioned and prepared for analysis. A portion can be fixed with glutaraldehyde. The nerve segments may be postfixed in 1% osmium [4% sucrose, 1.5% $K_3Fe(CN)_6$ in cacodylate buffer], dehydrated through ethanol (50-100%), and placed in propylene oxide before embedding in Epon 812 such that the cut faces of the nerve incised at the time of biopsy are oriented toward the face of the block. After curing, 1-μm sections may be cut and stained with paraphenylenediamine to enhance the contrast of myelin for quantitative computer-assisted light microscopic morphometric analysis. The largest fascicle meeting criteria from cross-sectional area (>/=100,000 μm$^2$), fixation, and mechanical distortion (6% endoneurial area) may be selected for light microscopic morphometric analysis. The selected fascicle may be digitally imaged at 400× and analyzed for total endoneurial area, number of myelinated fibers, and total axon areas of each myelinated fiber by a semiautomated image analysis system. The fiber count (all fibers in the fascicle) and fascicular area (in square micrometers) may be determined. Fascicular fiber density may be obtained in the standard manner by dividing the total fiber count by total fascicular area and multiplying by 1,000,000. The value may be expressed in fibers per square millimeter.

Determining electrophysiology parameters and obtaining and analyzing nerve biopsies are described, e.g., in Bril and Perkins, Diabetes Care, Vol 25. No. 11, November 2002, pp 2048-2052. For standards in electrophysiology methods, see Bolton et al., The Canadian Journal of Neurological Sciences, 2000; 27:288-291.

Immunoglobulin Products

The term "immunoglobulin product" is intended to mean any polyclonal antibody fraction. In this regard, the term "antibody" may be interchangeably used with the term "immunoglobulin". The immunoglobulin product may be derived from mammalian, preferably human, plasma. In certain embodiments, the plasma of multiple (generally 1000 or more) healthy donors is pooled and optionally further processed. The term "healthy individual" means an individual who meets the current (at the time of donation) standard eligibility criteria for donating blood, bearing in mind that such eligibility criteria are subject to continuous improvement and change. In some embodiments, the immunoglobulin fraction is enriched from the pooled plasma. Preferably, the immunoglobulin is purified from the pooled plasma. More preferably, the immunoglobulin is purified and concentrated. In various embodiments, purified and concentrated immunoglobulin G (IgG) is used.

In certain embodiments, the immunoglobulin product may contain traces of immunoglobulins of different Ig classes such as IgA or IgM. In one embodiment, the IgA concentration is 50 μg or less per 100 mg immunoglobulin. In a preferred embodiment, the IgA concentration is 25 μg or less per 100 mg immunoglobulin. Low IgA is desirable in order to avoid adverse events in patients with IgA deficiency. In one embodiment, the IgM concentration is 10 μg or less per 100 mg immunoglobulin. In a preferred embodiment, the IgM concentration is 5 μg or less per 100 mg immunoglobulin. In various embodiments, the immunoglobulin product exhibits a purity of the protein fraction of >90% IgG, more preferably >95% IgG, even more preferably >98% IgG. In various embodiments, the immunoglobulin product exhibits an immunoglobulin monomer and dimer content of >90%, more preferably >95%, even more preferably >98%. The provided product preferably exhibits a natural IgG subclass distribution. In one embodiment, the immunoglobulin subclass distribution in the immunoglobulin product is 62-74% IgG1, 22-34% IgG2, 2-5% IgG3 and 1-3% IgG4. The immunoglobulin product may contain additional ingredients such as stabilizers, for example amino acids such as proline or glycine, or sucrose, maltose, sorbitol, albumin nicotinamide, PEG, polysorbate 80, or others. Preferred stabilizers are amino acids, in particular proline. In various embodiments, the immunoglobulin product contains 10-30% (w/v) immunoglobulin. In certain embodiments, the immunoglobulin product is provided as a solution containing at least 10% (w/v) immunoglobulin, more preferably at least 15% (w/v) immunoglobulin, most preferably about 20% (w/v) immunoglobulin. The immunoglobulin product may also contain about 25% or even 30% (w/v) immunoglobulin. The immunoglobulin product is virus-safe for enveloped viruses (e.g., HIV, HBV and HCV) and non-enveloped viruses (e.g., HAV and parovirus B19).

The immunoglobulin product may be provided as a liquid product or a lyophilized product. In a preferred embodiment, the immunoglobulin product is provided as a liquid product. Such liquid products are ready-for-use, i.e., it is not necessary to reconstitute the product prior to administration. Liquid products are convenient to use, as no reconstitution is required. Therefore, liquid products are particularly suitable for self-administration by patients.

The provided immunoglobulin products are storage-stable over extended time periods. In one embodiment, the immunoglobulin product is storage-stable in liquid form for at least 12 months when stored at a maximum temperature of 25° C. In a preferred embodiment, the immunoglobulin product is storage-stable in liquid form for at least 24 months when stored at a maximum temperature of 25° C. In a further preferred embodiment, the immunoglobulin product is storage-stable in liquid form for at least 30 months when stored at a maximum temperature of 25° C. The term "storage-stability" as used herein refers to the maintenance of one or more features of the immunoglobulin product over the storage period. For example, storage-stability is indicated by the absence of immunoglobulin aggregation. In one embodiment, the immunoglobulin monomer and dimer content of the immunoglobulin product remains above 95% during storage for at least 12 months when stored at a maximum temperature of 25° C. In a further embodiment, the immunoglobulin monomer and dimer content of the immunoglobulin product remains above 95% during storage for at least 24 months when stored at a maximum temperature of 25° C. In one embodiment, the immunoglobulin monomer and dimer content of the immunoglobulin product remains above 98% during storage for at least 12 months when stored at a maximum temperature of 25° C. In a further embodiment, the immunoglobulin monomer and dimer content of the immunoglobulin product remains above 98% during storage for at least 24 months when stored at a maximum temperature of 25° C.

A preferred immunoglobulin product is a product for subcutaneous administration (SCIG). The term "subcutaneous immunoglobulin G", abbreviated SCIG, means a therapeutic preparation of pooled immunoglobulin G formulated for subcutaneous administration. SCIG also denotes a product as well as a preferred route of administration (subcutaneous administration). In certain embodiments, the SCIG is VIVAGLOBIN® or HIZENTRA® (both manufactured and sold by CSL Behring).

The immunoglobulin product may also be a product for intravenous administration (IVIG). IVIG denotes a product, as well as the preferred route of administration (intravenous administration). In certain embodiments, the IVIG is PRIVIGEN® or SANDOGLOBULIN®/CARIMUNE® (both manufactured and sold by CSL Behring).

Medical Uses and Dosing Schemes

The present invention provides a method for diagnosing CIDP with non-axonal damage in a patient. The invention further provides a method for diagnosing CIDP with mild damage in a patient. The invention further provides an immunoglobulin product for use in a method of treating CIDP, wherein the method comprises selecting a patient who has non-axonal damage for treatment with the immunoglobulin product. The invention further provides an immunoglobulin product for use in a method of treating CIDP, wherein the method comprises selecting a patient who has mild axonal damage for treatment with the immunoglobulin product. In one embodiment, the diagnosis or the selection of a patient involves an electrophysiology measurement. The electrophysiology measurement may involve (i) supramaximal nerve stimulation using a stimulation electrode, and (ii) recording the amplitude of the compound muscle action potential using a recording electrode.

The patient may be selected or diagnosed based on a pre-determined cut-off amplitude for the compound muscle action potential. The electrophysiology measurement may be carried out at the wrist or at the foot. In a preferred embodiment, the electrophysiology measurement is carried out at the foot.

The electrophysiology measurements may be carried out at the ulnar motor nerve, at the median motor nerve, and/or at the peroneal motor nerve. In one embodiment, the electrophysiology measurements are carried out at the ulnar motor nerve at the wrist. In one embodiment, the electrophysiology measurements are carried out at the median motor nerve at the wrist. In a preferred embodiment, the electrophysiology measurements are carried out at the peroneal motor nerve at the foot.

The distance between the stimulation electrode and the recording electrode may be between 55 and 75 mm, preferably 65 mm for the ulnar motor nerve. The distance between the stimulation electrode and the recording electrode may be between 60 and 80 mm, preferably 70 mm for the median motor nerve. The distance between the stimulation electrode and the recording electrode may be between 80 and 100 mm, preferably 90 mm for the peroneal motor nerve.

In one embodiment, the electrophysiology measurement is carried out while the temperature is maintained at a certain level. For example, the electrophysiology measurement is carried out at a temperature of between 30-36° C., preferably between 32-34° C. In another embodiment, the temperature is maintained above 30° C. during the measurement. In a further embodiment, the temperature is maintained above 31° C. during the measurement. In yet a further embodiment, the temperature is maintained above 32° C. during the measurement.

The present invention provides an immunoglobulin product for use in treating patients with CIDP exhibiting an amplitude>1 mV at the foot. The present invention provides an immunoglobulin product for use in treating patients with CIDP exhibiting an amplitude>1.5 mV at the foot. The present invention provides an immunoglobulin product for use in treating patients with CIDP exhibiting an amplitude>2 mV at the foot.

The present invention provides an immunoglobulin product for use in treating patients with CIDP exhibiting an amplitude>2 mV at the wrist. The present invention provides an immunoglobulin product for use in treating patients with CIDP exhibiting an amplitude>3 mV at the wrist. The present invention provides an immunoglobulin product for use in treating patients with CIDP exhibiting an amplitude>4 mV at the wrist.

The present invention provides an immunoglobulin product for use in treating patients with CIDP exhibiting an amplitude>1 mV at the foot and >2 mV at the wrist. The present invention provides an immunoglobulin product for use in treating patients with CIDP exhibiting an amplitude>1.5 mV at the foot and >3 mV at the wrist. The present invention provides an immunoglobulin product for use in treating patients with CIDP exhibiting an amplitude>2 mV at the foot and >4 mV at the wrist.

In one embodiment, CIDP patients exhibiting >1 mV amplitude at the foot, and/or >2 mV amplitude at the wrist are considered as patients with non-axonal damage or mild axonal damage. In one embodiment, CIDP patients exhibiting >1.5 mV amplitude at the foot, and/or >3 mV amplitude at the wrist are considered as patients with non-axonal damage or mild axonal damage. In one embodiment, CIDP patients exhibiting >2 mV amplitude at the foot, and/or >4 mV amplitude at the wrist are considered as patients with non-axonal damage or mild axonal damage. In a preferred embodiment, CIDP patients exhibiting >1 mV amplitude at the foot, and/or >2 mV amplitude at the wrist are considered as patients with non-axonal damage or mild axonal damage.

The above described electrophysiology parameter may vary depending on factors other than CIDP. For example, they may vary depending on the age of the patient. In particular, with increasing age, the threshold of the amplitude for determining axonal damage may decrease. In one embodiment, CIDP patients above age 60 exhibiting an amplitude of >0.5 mV for the foot, and/or >1 mV for the wrist can be considered as patients with non-axonal damage or mild axonal damage. In one embodiment, CIDP patients above age 40 exhibiting an amplitude of >1 mV for the foot, and/or >2 mV for the wrist can be considered as patients with non-axonal damage or mild axonal damage. In one embodiment, CIDP patients above age 30 exhibiting an amplitude of >1.5 mV for the foot, and/or >3 mV for the wrist can be considered as patients with non-axonal damage or mild axonal damage. In one embodiment, CIDP patients above age 20 exhibiting an amplitude of >2 mV for the foot, and/or >4 mV for the wrist can be considered as patients with non-axonal damage or mild axonal damage.

The present invention also provides an immunoglobulin product for use in treating patients with CIDP exhibiting an amplitude that is at least 50% of the mean amplitude measured in a healthy subject. The present invention also provides an immunoglobulin product for use in treating patients with CIDP exhibiting an amplitude that is at least 40% of the mean amplitude measured in a healthy subject. The present invention also provides an immunoglobulin product for use in treating patients with CIDP exhibiting an amplitude that is at least 30% of the mean amplitude measured in a healthy subject. The present invention also provides an immunoglobulin product for use in treating patients with CIDP exhibiting an amplitude that is at least 20% of the mean amplitude measured in a healthy subject. The present invention also provides an immunoglobulin product for use in treating patients with CIDP exhibiting an amplitude that is at least 10% of the mean amplitude measured in a healthy subject.

Different healthy subjects may display a certain variation in their amplitudes upon supramaximal stimulation. Accordingly, the mean amplitude may exhibit a certain standard deviation. In one embodiment, the immunoglobulin product is for use in treating patients with CIDP exhibiting an amplitude that is at least 50% of the mean amplitude measured in a healthy subject minus the standard deviation. Thus, the cut-off amplitude is 50% of the lower limit of the mean amplitude in a healthy subject. In one embodiment, the immunoglobulin product is for use in treating patients with CIDP exhibiting an amplitude that is at least 40% of the mean amplitude measured in a healthy subject minus the standard deviation. Thus, the cut-off amplitude is 40% of the lower limit of the mean amplitude in a healthy subject.

The mean amplitude may also vary depending on the age of the subjects analyzed. Accordingly, in order to minimize age-related variation, a CIDP patient may be considered eligible for treatment with an immunoglobulin product in case the amplitude measured in said patient is at least 50% of the mean amplitude measured in a healthy subject minus the standard deviation, wherein the healthy subject is from the same age group as the patient. In another embodiment, the amplitude measured in said patient is at least about 40% of the mean amplitude measured in a healthy subject of the same age group, minus the standard deviation. Age groups may, e.g., be defined as patients/subjects at an age of 10-20 years, 20-30 years, 30-40 years, 40-50 years, 50-60 years, 60-70 years and 70-80 years.

Patients can also be identified as suffering from CIDP with non-axonal damage by diagnosing patients using nerve biopsies.

Also provided is a method for treating patients with CIDP with non-axonal damage, wherein the method comprises administering a therapeutically effective amount of immunoglobulin product to a patient in need thereof. Further provided is a method for treating patients with CIDP with mild axonal damage, wherein the method comprises administering a therapeutically effective amount of immunoglobulin product to a patient in need thereof. CIDP patients with non-axonal damage and mild axonal damage can be selected/diagnosed based on the electrophysiology measurements and the cut-off amplitudes provided herein. Alternatively, the patients may be selected/diagnosed by nerve biopsy.

The dosing schemes described below are particularly efficacious in patients with CIDP exhibiting the electrophysiology parameters provided and described herein.

The dosing schemes described below are also particularly efficacious in patients suffering from CIDP with non-axonal damage or mild axonal damage. Accordingly, in one embodiment, these dosing schemes are intended for the treatment of CIDP with non-axonal damage. In another embodiment, these dosing schemes are intended for the treatment of CIDP with mild axonal damage.

The term "fixed dose" as used herein refers to a particular weight-based dose that can be administered to all patients. By using such a fixed dose, no individual dose adjustment is required.

In one embodiment, the immunoglobulin product is to be administered at a fixed dose selected from the range of 0.1-1 g/kg patient weight, or a fixed dose of 0.2 g/kg patient weight or a fixed dose of 0.4 g/kg patient weight per 5-10 days, per 6-8 days or per week.

Provided herein is an immunoglobulin product for use in the treatment of chronic inflammatory demyelinating polyneuropathy, wherein the immunoglobulin product is to be administered at a fixed dose selected from the range of 0.1-1 g/kg patient weight per 5-10 days. Further provided is an immunoglobulin product for use in the treatment of chronic inflammatory demyelinating polyneuropathy, wherein the immunoglobulin product is to be administered at a fixed dose selected from the range of 0.1-1 g/kg patient weight per 6-8 days. Further provided is an immunoglobulin product for use in the treatment of chronic inflammatory demyelinating polyneuropathy, wherein the immunoglobulin product is to be administered at a fixed dose selected from the range of 0.1-1 g/kg patient weight per week.

Provided herein is an immunoglobulin product for use in the treatment of chronic inflammatory demyelinating polyneuropathy, wherein the immunoglobulin product is to be administered at a fixed dose of 0.2 g/kg patient weight per 5-10 days. Further provided is an immunoglobulin product for use in the treatment of chronic inflammatory demyelinating polyneuropathy, wherein the immunoglobulin product is to be administered at a fixed dose of 0.2 g/kg patient weight per 6-8 days. Further provided is an immunoglobulin product for use in the treatment of chronic inflammatory demyelinating polyneuropathy, wherein the immunoglobulin product is to be administered at a fixed dose of 0.2 g/kg patient weight per week.

Provided herein is an immunoglobulin product for use in the treatment of chronic inflammatory demyelinating polyneuropathy, wherein the immunoglobulin product is to be administered at a fixed dose of 0.4 g/kg patient weight per 5-10 days. Further provided is an immunoglobulin product for use in the treatment of chronic inflammatory demyelinating polyneuropathy, wherein the immunoglobulin product is to be administered at a fixed dose of 0.4 g/kg patient weight per 6-8 days. Further provided is an immunoglobulin product for use in the treatment of chronic inflammatory demyelinating polyneuropathy, wherein the immunoglobulin product is to be administered at a fixed dose of 0.4 g/kg patient weight per week.

For the patient groups defined herein by the described electrophysiology parameters and/or by nerve biopsies, i.e., patients with non-axonal damage or mild axonal damage, the preferred weekly dose is 0.4 g/kg.

Further provided is a method for treating chronic inflammatory demyelinating polyneuropathy (CIDP), wherein the method comprises administering an immunoglobulin product to a patient in need thereof, wherein the immunoglobulin product is to be administered at a fixed dose selected from the range of 0.1-1 g/kg patient weight per 5-10 days. The individual dosing schemes listed herein for the immunoglobulin product for use in the treatment of chronic inflammatory demyelinating polyneuropathy equally apply to any methods for treating chronic inflammatory demyelinating polyneuropathy.

The immunoglobulin product may be administered in any suitable way. In one embodiment, the immunoglobulin product is administered intravenously. In a preferred embodiment, the immunoglobulin product is administered subcutaneously. Subcutaneous administration may be carried out by subcutaneous bolus injection or subcutaneous infusion. Subcutaneous infusion may be carried out by using an infusion pump. Subcutaneous administration of immunoglobulin products is advantageous as it results in low peak to trough ratios in patients. Accordingly, by subcutaneous administration, the administered IgG remains at a relatively stable level in the patient. Such stable levels ensure an optimal treatment effect.

In a further preferred embodiment, the patient self-administers the immunoglobulin product. Self-administration enhances patient compliance. No visit of a treatment center is required. Further, the administration can be incorporated into the patient's daily life according to the patient's convenience.

The entire fixed dose of immunoglobulin product may be administered at once, i.e., without any discontinuation of administration. The dose may also be divided into several portions and these portions may be administered individually with breaks in between. Such stepwise administration may be carried out over the course of one day or over the course of several days. In one embodiment, a fixed dose of the immunoglobulin product is divided into two or more portions and these portions are administered over the course of 1-7 days. Accordingly, the patient may individually decide whether s/he prefers to receive the entire dose at once or to receive the dose in several portions over the course of one or several days.

In one embodiment, the fixed dose of the immunoglobulin product is to be administered over the course of 1-7 days. In a further embodiment, the fixed dose of the immunoglobulin product is to be administered over the course of one day. In a further embodiment, the fixed dose of the immunoglobulin product is to be administered over the course of two days. In a further embodiment, the fixed dose of the immunoglobulin product is to be administered over the course of three days. In a further embodiment, the fixed dose of the immunoglobulin product is to be administered over the course of four days. In a further embodiment, the fixed dose of the immunoglobulin product is to be administered over the course of five days. In a further embodiment, the fixed dose of the immunoglobulin product is to be administered over the course of six days. In a further embodiment, the fixed dose of the immunoglobulin product is to be administered over the course of seven days.

In another embodiment, two or more fixed doses are combined and are administered in accordingly extended intervals. Upon such combination, the total dose per time is likewise maintained. For example, if the total weekly dose is 0.2 g/kg patient weight, 0.4 g/kg could be administered biweekly.

In one embodiment, the fixed dose of the immunoglobulin product is doubled and it is to be administered every 14 days. In a further embodiment, the fixed dose of the immunoglobulin product is tripled and it is to be administered every 21 days. In a further embodiment, the fixed dose of the immunoglobulin product is quadrupled and it is to be administered every 28 days.

In one embodiment, the immunoglobulin product is to be administered at a flexible dosing regimen.

In such a flexible dosing regimen, the total dose of immunoglobulin product administered over time is kept constant. Therefore, irrespective of whether administration occurs less frequent (increased dosing intervals) or more frequent (reduced dosing intervals), the same amount of immunoglobulin product is administered over time. The total weekly dose is maintained, although the dosing interval may be longer or shorter than one week. The invention is further described by the following embodiments:

The recommended subcutaneous dose is 0.2 to 0.4 g/kg (1 to 2 mL/kg) body weight per week.

Initiate therapy with immunoglobulin product 1 week after the last IGIV infusion.

Provided the total weekly dose is maintained, any dosing interval from daily up to biweekly (every 2 weeks) can be used and will result in systemic serum IgG exposure that is comparable to the weekly immunoglobulin product treatment.

Biweekly: Multiply the calculated immunoglobulin product weekly dose by 2.

Frequent dosing (2 to 7 times per week): Divide the calculated weekly dose by the desired number of times per week (e.g., for 3 times per week dosing, divide weekly dose by 3).

Hence, the provided treatment gives patients great flexibility regarding the administration schedule of the drug.

The provided treatment may be carried out over extended time periods ranging from several weeks to years. In one embodiment, the treatment is carried out for at least 3 months. In a further embodiment, the treatment is carried out for at least 6 months. In another embodiment, the treatment is carried out for at least 12 months. In yet another embodiment, the treatment is carried out for at least 24 months.

The provided treatment is well tolerated. Upon subcutaneous administration of low doses of immunoglobulin, e.g., 0.2 g/kg patient weight, local reactions at the site of injection occur only at low frequency.

Patients not responding to immunoglobulin treatment may undergo an individual dose adjustment in order to experience a treatment effect.

Treatment Effects

The provided treatment may result in various treatment effects in patients suffering from CIDP with non-axonal damage. These effects include: INCAT score, R-ODS score, Mean grip strength, MRC sum score (8 muscle groups) and electrophysiology parameters: distal and proximal latencies, compound action potential (CMAP) amplitudes, nerve conduction velocities, and conduction block in 3 motor nerves. These effects can be achieved with any of the treatments provided herein.

The INCAT score is a 10-point scale that covers the functionality of legs and arms, and has been successfully used to measure treatment effects in various CIDP studies. Scores for arm disability range from 0 ("No upper limb problems") to 5 ("Inability to use either arm for any purposeful movement"), and scores for leg disability range from 0 ("Walking not affected") to 5 ("Restricted to wheelchair, unable to stand and walk a few steps with help"). The INCAT (total) score is the sum of these 2 scores and ranges from 0 to 10. For the "adjusted" INCAT score, changes in the function of the upper limbs from 0 (normal) to 1 (minor symptoms) or from 1 to 0 are not recorded as deterioration or improvement because these changes are not considered clinically significant (Hughes R et al, Ann Neurol. 2001; 50(2): 195-201; Hughes R A et al., Lancet Neurol. 2008; 7(2): 136-144; Hughes R A, Expert Rev Neurother. 2009; 9(6): 789-795).

The R-ODS centile score is an outcome measure that captures activity and social participation in subjects with Guillain-Barré Syndrome, CIDP, and monoclonal gammopathy of uncertain significance related polyneuropathy (MGUSP) (van Nes S I et al. Neurology. 2011; 76(4): 337-345). This Rasch analysis-based 24-item questionnaire covers a wide range of tasks of daily life ranging from easiest tasks such as "reading a newspaper/book" and "eating" to the most difficult tasks such as "running" or "standing for hours" that are each to be rated as "impossible to perform", "performed with difficulties", or "easily performed".

The Mean Grip Strength may be measured by Martin Vigorimeter. The hand-held Vigorimeter from Martin (Tuttlingen, Germany) is a device that measures the strength of small muscles in the hand; i.e., grip strength. Subjects squeeze a rubber bulb lying between the palm of the hand and the thumb and index fingers. The pressure is recorded via a rubber tube on a nanometer and expressed in kilopascal. At each assessment, the subjects squeeze 3 times with each hand. The mean grip strength of each hand is determined.

An adapted version of the MRC sum score (Léger J M et al, Brain. 2001; 124(Pt 1): 145-153) may be used. MRC sum score grades could range from 0 ("No visible contraction") to 5 ("Normal"). The following 8 bilateral muscle pairs may be assessed, and individual muscle scores and the sum score are documented: shoulder abduction, elbow flexion, wrist extension, index finger abduction, hip flexion, knee extension, foot dorsiflexion, great toe dorsiflexion.

Electrophysiology parameters may be assessed. Three motor nerves (2 in the arm, 1 in the leg) are measured: median, ulnar, and peroneal. The stimulation points are as follows: ulnar nerve: wrist, above elbow; median nerve: wrist, elbow; peroneal nerve: ankle, below fibular head, lateral popliteal fossa.

In one embodiment, the provided treatment results in an improvement of one or more of INCAT score, R-ODS score, Mean grip strength, MRC sum score and electrophysiology parameters by at least 10% over placebo treatment. In a further embodiment, the provided treatment results in an improvement of one or more of INCAT score, R-ODS score, Mean grip strength, MRC sum score and electrophysiology parameters by at least 20% over placebo treatment. In a further embodiment, the provided treatment results in an improvement of one or more of INCAT score, R-ODS score, Mean grip strength, MRC sum score and electrophysiology parameters by at least 30% over placebo treatment. In a further embodiment, the provided treatment results in an improvement of one or more of INCAT score, R-ODS score, Mean grip strength, MRC sum score and electrophysiology parameters by at least 40% over placebo treatment. In a further embodiment, the provided treatment results in an improvement of one or more of INCAT score, R-ODS score, Mean grip strength, MRC sum score and electrophysiology parameters by at least 50% over placebo treatment. In a further embodiment, the provided treatment results in an improvement of one or more of INCAT score, R-ODS score, Mean grip strength, MRC sum score and electrophysiology parameters by at least 60% over placebo treatment. In a further embodiment, the provided treatment results in an improvement of one or more of INCAT score, R-ODS score, Mean grip strength, MRC sum score and electrophysiology parameters by at least 70% over placebo treatment. In a further embodiment, the provided treatment results in an improvement of one or more of INCAT score, R-ODS score, Mean grip strength, MRC sum score and electrophysiology parameters by at least 80% over placebo treatment. In a further embodiment, the provided treatment results in an improvement of one or more of INCAT score, R-ODS score, Mean grip strength, MRC sum score and electrophysiology parameters by at least 90% over placebo treatment. In a further embodiment, the provided treatment results in an improvement of one or more of INCAT score, R-ODS score, Mean grip strength, MRC sum score and electrophysiology parameters by at least 100% over placebo treatment.

The provided treatment results in a reduction of the CIDP relapse rate in CIDP patients. In one embodiment, the provided treatment results in a reduction in the relapse rate of more than 30%, preferably more than 40%, more preferably more than 50%, or even more than 60% or even more than 70% when compared to placebo.

In one embodiment, the provided treatment with a fixed dose of 0.4 g/kg weekly results in a reduction in the relapse rate of more than 30% when compared to placebo. In one embodiment, the provided treatment with a fixed dose of 0.4 g/kg weekly results in a reduction in the relapse rate of more than 40% when compared to placebo. In one embodiment, the provided treatment with a fixed dose of 0.4 g/kg weekly results in a reduction in the relapse rate of more than 50% when compared to placebo. In one embodiment, the provided treatment with a fixed dose of 0.4 g/kg weekly results in a reduction in the relapse rate of more than 60% when compared to placebo. In one embodiment, the provided treatment with a fixed dose of 0.4 g/kg weekly results in a reduction in the relapse rate of more than 70% when compared to placebo.

The provided treatment results in an increase of patients who do not experience a CIDP relapse. In one embodiment, the provided treatment results in an increase of patients who do not experience a CIDP relapse of more than 30%, preferably more than 40%, more preferably more than 60%, or even more than 80% when compared to placebo.

EXAMPLES

Background:

Chronic Inflammatory Demyelinating Polyneuropathy (CIDP) is an immune mediated disease starting with functional impairment and demyelination; in later stages, axonal degeneration may occur. Nerve conduction measurements are standard procedures and can be carried out by a skilled person based on his/her common general knowledge. The following protocol is an example for such a nerve conduction measurement protocol.

General Protocol:
1. General Requirements
The following 3 nerves should be tested on the right side:

| Nerve Name | Stimulation sites |
|---|---|
| Ulnar Motor Nerve (*N. ulnaris*) | wrist above elbow |
| Median Motor Nerve (*N. medianus*) | wrist elbow |
| Peroneal Motor Nerve (*N. peronaeus*) | ankle below fibular head lateral popliteal fossa |

The side tested should be recorded on the tracing. The parameters to be measured should be: Distal and proximal onset latencies distal and proximal amplitudes segmental conduction velocities.

2. Nerve Conduction Studies Equipment

Commercially available electromyographic equipment with the following features: Electrical stimulator with constant current or constant voltage, calibration signal output—the EMG instrument should generate and print out a motor calibration signal. The same equipment should be used throughout the study.

2.1 Temperature Probe

Surface thermistors probe or skin temperature tester for recording skin temperature. It is preferable that the thermistor probe be connected to the EMG instrument so the temperature recorded at the beginning and end of each testing will be displayed on the tracing. If a separate thermistor is used, then the temperature must be manually entered on the tracing.

2.2 Electrodes

For example: Surface recording electrodes for motor nerve conduction studies: 9-10 mm disc electrodes; 4×7 mm (area) adhesive recording electrodes (Ag/AgCl), surface stimulating electrodes, or strap or disc ground electrodes.

The electrode gel used must have appropriate conductive properties for nerve conduction studies. Ultrasound gel and other non-electrolyte gels should not be used.

2.3 Temperature Control Equipment

Warming water bath, heating pads, heating blanket, or radiant lamp should be available for raising and maintaining skin temperature as required per protocol.

3. Laboratory Procedures 3.1 Motor Nerve Conduction Studies—Parameter Settings

Filters: Low Frequency: 2 Hz; High Frequency: 5 kHz-10 kHz

Gain: 0.5 mV-5 mV/div

The gain sensitivity should be set appropriately so the motor responses are displayed over at least two amplitude divisions on the printout.

Sweep Speed: 3-5 ms/Div (Increase if Necessary)

The same sweep speed settings for latency measurements should be used at subsequent visits for the same subject. The sweep speed should be set appropriately so the entire proximal motor curves are displayed on the screen.

3.2 Calibration Signals

A motor calibration signal should be performed at the beginning of each set of nerve conduction studies for each subject (FIG. 1).

3.3 Skin Preparation

The skin at the recording and stimulation sites should be uniformly lightly abraded with a commercial abrasion material and cleaned with alcohol before each nerve conduction testing. Ensure that the skin is dry before applying the electrodes. Same skin preparation should be performed at subsequent visits.

3.4 Temperature Measurements

Ideally, the limb temperature is measured at the beginning and end of each nerve conduction study. The temperature at start and end should be recorded on the hard copy of each nerve tracing. For the median and ulnar nerve conduction studies, temperature should be measured in the right mid forearm. The minimum temperature is >32° C. For the peroneal nerve conduction studies, temperature is ideally measured in the right lower leg. The minimum temperature is >31° C.

The temperature should be monitored, adjusted and maintained within specified range with a warm water bath, heating pads, heating blanket or a radiant lamp throughout testing. Radiant lamp should be used at low setting to allow gradual and deep warming of the limb.

3.5 Distance Measurements

All distances should be measured to the nearest 1 mm and recorded on the tracings even if there is no response. Distance should be measured along the course of the nerve with the same limb position used for stimulation. Distal distances should be measured from the stimulating cathode at the distal site to the active recording electrode. Proximal distances should be measured between the stimulating cathode of the distal and proximal sites.

Distal distances used may be between 80-100 mm, preferably 90 mm for peroneal motor; 60-80 mm, preferably 70 mm and 55-75 mm, preferably 65 mm for median and ulnar motor, respectively. For the peroneal motor nerve studies, distance between below fibular head and lateral popliteal fossa should be at least 80 mm.

Distance measurements represent the highest chance of error in electrophysiological testing. To maximize consistency of amplitude measurement, distances used should be approximately the same at subsequent visits.

3.6 Nerve Stimulation

All nerves are stimulated with an electrical stimulator. The duration of stimulus current may be 0.1 to 0.2 ms and may be increased if necessary. The stimulation rate may be 1/sec. The intensity of stimulation should be increased in steps until a maximal evoked response is obtained. The stimulus intensity then will be increased by 20-30% above maximal stimulation and adjusted along with duration to elicit a well-defined supramaximal motor response. Stimulation intensity used should be clearly indicated on each tracing at each stimulation site. Excessive stimulation should be avoided.

3.7 Waveform Measurement

Gain and sweep speed settings should be selected appropriately so the entire curves are displayed on the print out.

3.7.1 Amplitude Measurements

Figure 2:
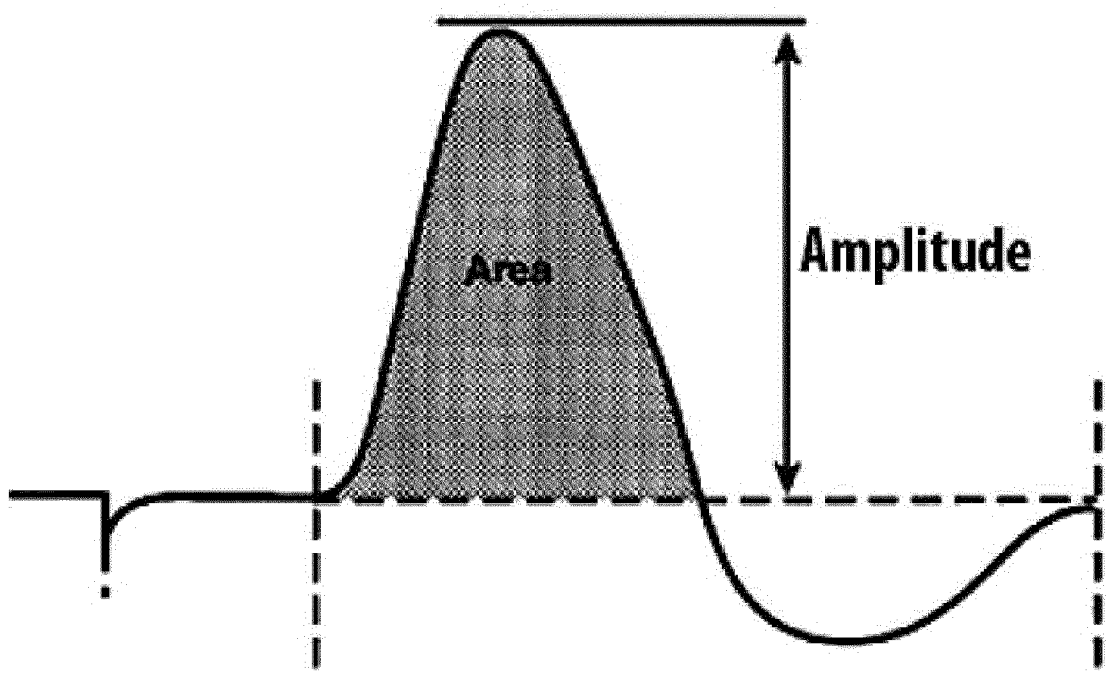
FIG. 2: Motor response Amplitude measurement. Measured from Baseline to Peak.

Motor responses should be displayed over 2 divisions (FIG. 2).

3.7.2 Latency Measurements

Figure 3:
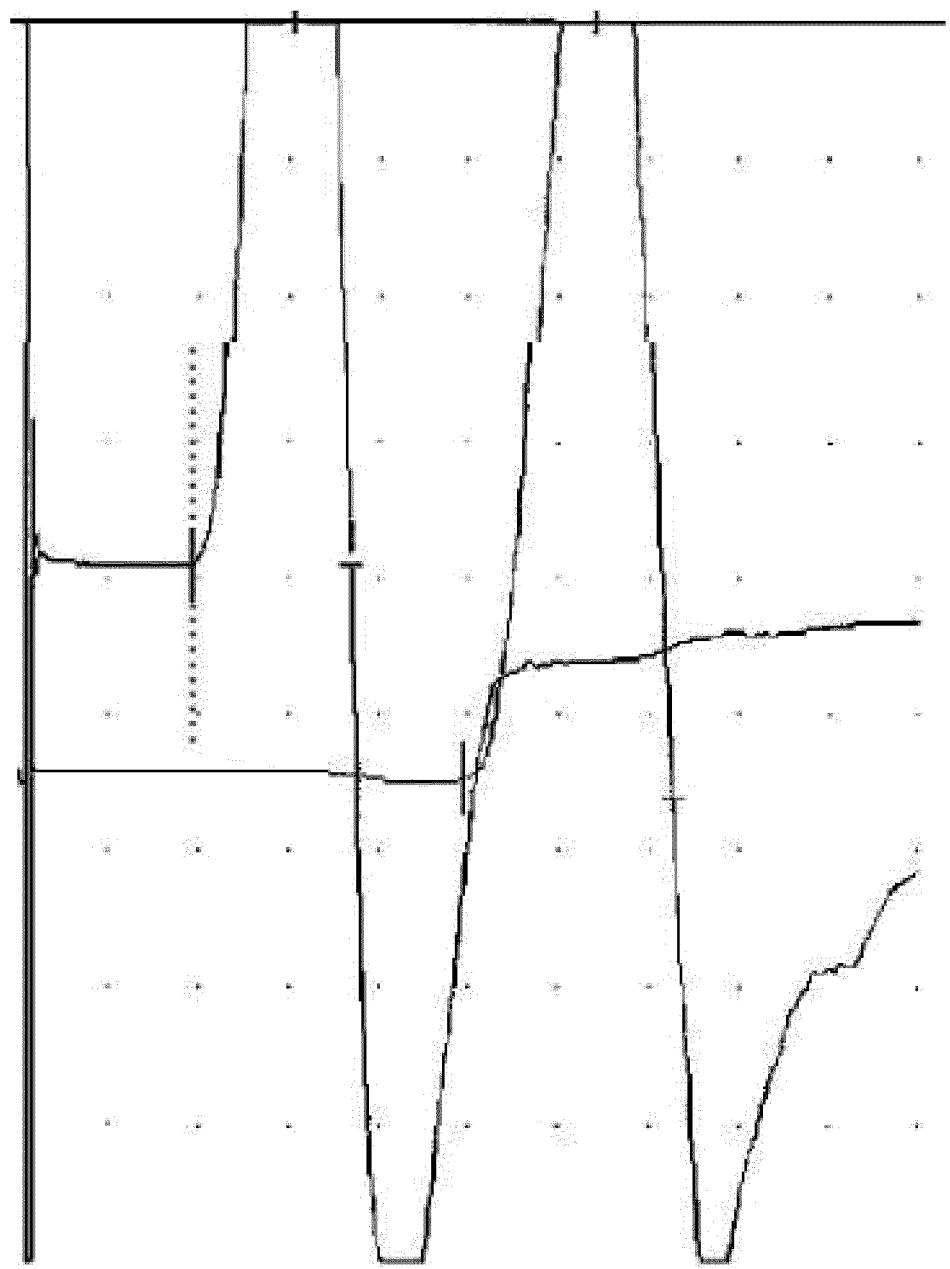
FIG. 3: Motor Response Latency Measurement. Measured at the onset of the initial negative peak using a high gain setting.

Motor latencies should be rounded to the nearest 0.1 ms. The latency is measured at the onset of the same M wave obtained after supramaximal stimulation using a high gain setting that clips the peak of the M wave. This results in a sharper take-off and more clearly defined onset (FIG. 3; dotted line).

The high gain setting used for clipped curves should be 0.5 mV/div. For very low amplitude motor responses, latency should be measured at the onset of the waveform displayed over one or two divisions.

Each motor nerve conduction study should include two tracings: one showing the entire waveform for amplitude evaluation and the other showing the same M waveform but displayed at least at 0.5 mV/div gain setting with the peak of the M wave clipped for onset latency evaluation.

3.7.3 Conduction Velocity Calculation

Segmental conduction velocities may be calculated for motor responses. Conduction velocity should be recorded to the nearest 0.1 m/s.

Figure 4:
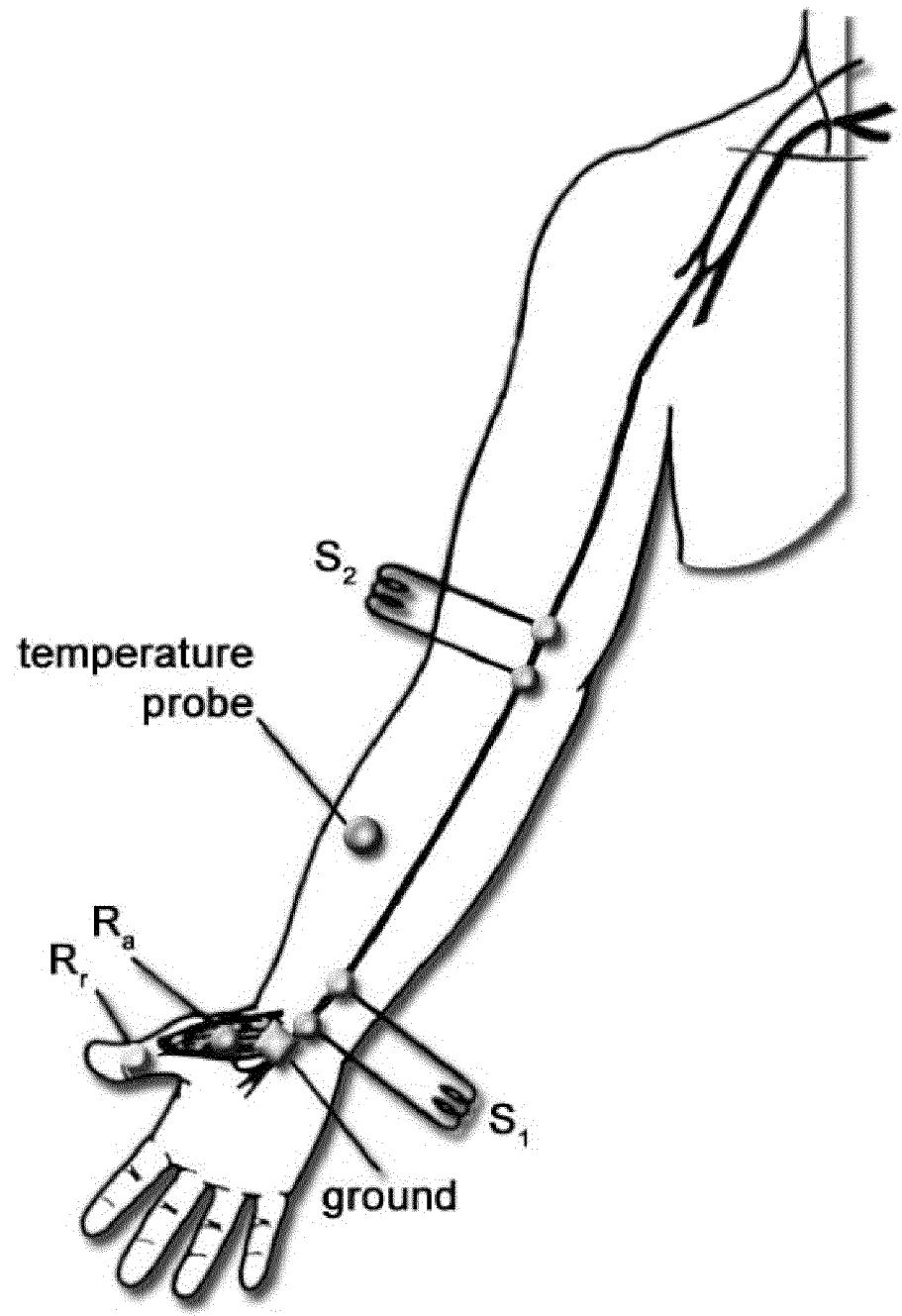
FIG. 4: Median Motor Nerve Conduction Study Placement of recording and stimulating electrodes. Ra=recording active electrode. Rr=recording reference electrode. Recording site: abductor pollicis *brevis* (APB). Stimulating site: S1: Wrist; S2: Elbow. Distal distance: 70 mm Temperature probe placed in the mid forearm.

4. Nerve Conduction Methodology
4.1 Median Motor Nerve Conduction Studies Set the filters for motor nerve conduction study. The sweep speed may be set at 3-5 ms/div (increase if necessary), and the gain may be set at 2-5 mV/div. Locate, lightly abrade and clean the skin at the recording and stimulating sites. Place the active recording electrode over the end-plate region of the abductor pollicis brevis muscle (APB) (FIG. 4). Place the reference electrode over the metacarpal-phalangeal joint of the thumb.

Place the ground electrode between the recording and stimulating electrodes. Record the temperature in mid forearm. Temperature should be maintained within the range specified, i.e. >32 C.

S1 Wrist: Place the stimulating cathode over the median nerve at the wrist, between the palmaris longus and flexor carpi radialis tendons, at 60-80 mm, preferably 70 mm proximal to the recording active electrode. Stimulate the nerve at the wrist to achieve a supramaximal response (M wave from the wrist).

S2 Elbow: Place the stimulating cathode over the median nerve at the elbow crease, medial to the biceps brachii tendon, over the palpable brachial artery. Stimulate the nerve at the elbow crease to achieve a supramaximal response (M wave from the elbow).

Place and check the cursors for amplitude (baseline-negative peak) at sensitivity, usually 2-5 mV/div, which shows the entire response, spread over 2 or 3 divisions. Increase the gain to 0.5 mV/div and adjust the cursors for latency at the onset of the clipped peak of each M wave. Measure and record the distances (wrist to APB electrode, elbow to wrist) to the nearest 1 mm. Measure and record the temperature in mid forearm.

4.2 Ulnar Motor Nerve Conduction Studies

Figure 5:
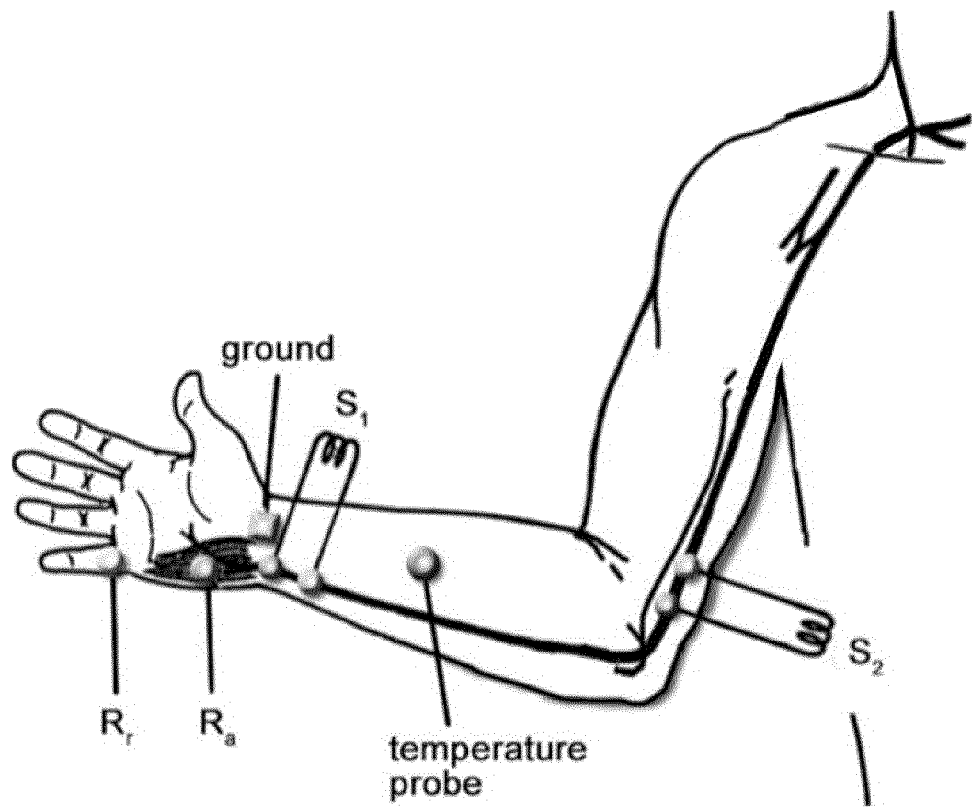
FIG. 5: Ulnar Motor Nerve Conduction Study Example for Placement of recording and stimulating electrodes. Recording site: abductor digiti minimi (ADM). Ra=recording active electrode. Rr=recording reference electrode. S1: Wrist; S2: Above Elbow. Distal distance: 65 mm Temperature probe placed in mid forearm. The flexed elbow position, 90 degrees from the horizontal is used. The same flexed elbow position must be used for distance measurement.
Figure 6:
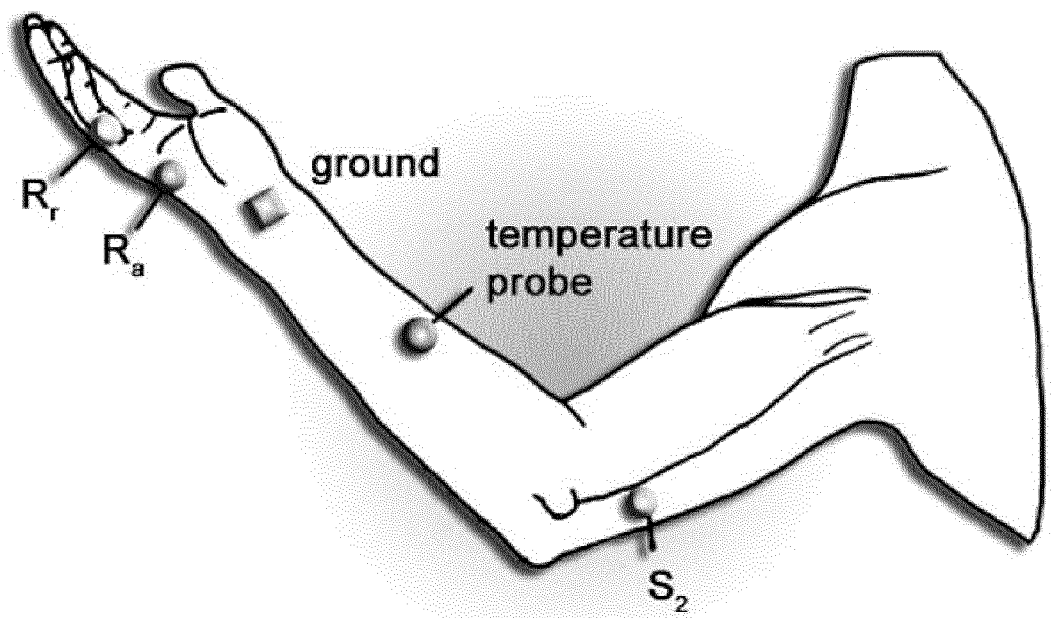
FIG. 6: Ulnar Motor Nerve Conduction Study Placement of recording and stimulating electrodes. Ra=recording active electrode. Rr=recording reference electrode. S2=Stimulating at Above Elbow. Forearm rotated outward and the elbow flexed, 90 degrees from the horizontal (palm facing upward). The flexed elbow position, 90 degrees from the horizontal is used. The same flexed elbow position must be used for distance measurement.

It is recommended that when performing the ulnar motor nerve conduction, the flexed elbow position of 90 degrees from the horizontal should be used. The same position also should be used for distance measurement to avoid discrepancy due to altering the position of the forearm. The same position should be used at subsequent visits (FIGS. 5 & 6).

Set the filters for motor nerve conduction study. The sweep speed may be set at 3-5 ms/div (increase if necessary), and the gain may be set at 2-5 mV/div. Locate, lightly abrade and clean the skin at the recording and stimulating sites. Place the active recording electrode over the end-plate region of the abductor digiti minimi muscle (ADM), at the ulnar dorsal border, just below the fifth metacarpal bone one-half way between the wrist crease and the crease of the fifth metacarpophalangeal joint. Place the reference electrode slightly distal to the fifth metacarpophalangeal joint, on the lateral surface of the fifth digit.

Place the ground electrode between the recording and stimulating electrodes. Record the temperature in the mid forearm. Temperature should be maintained within the range specified, i.e. >32° C.

S1 Wrist: Place the stimulating cathode over the ulnar nerve at the wrist, just radial to the flexor carpi ulnaris tendon, at 55-75 mm, preferably 65 mm proximal to the recording active electrode. Stimulate the nerve at the wrist to achieve a supramaximal response (M wave from the wrist).

S2 Above Elbow: With the forearm rotated outward and the elbow flexed 90 degrees from the horizontal, place the stimulating cathode along the ulnar nerve (3-4 cm distal to the medial epicondyle) and stimulate the nerve above the elbow to achieve a supramaximal response (M wave from above elbow).

Place and check the cursors for amplitude (baseline-negative peak) at sensitivity, usually 2-5 mV/div, which shows the entire response, spread over 2 or 3 divisions. Increase the gain to 0.5 mV/div and adjust the cursors for latency at the onset of the clipped peak of each M wave. Measure and record the distances (wrist to ADM electrode, above elbow to wrist) to the nearest 1 mm. The distance should be measured with the elbow flexed at 90 degrees. Measure and record the temperature in the mid forearm.

4.3 Peroneal Motor Nerve Conduction Studies

Figure 7:
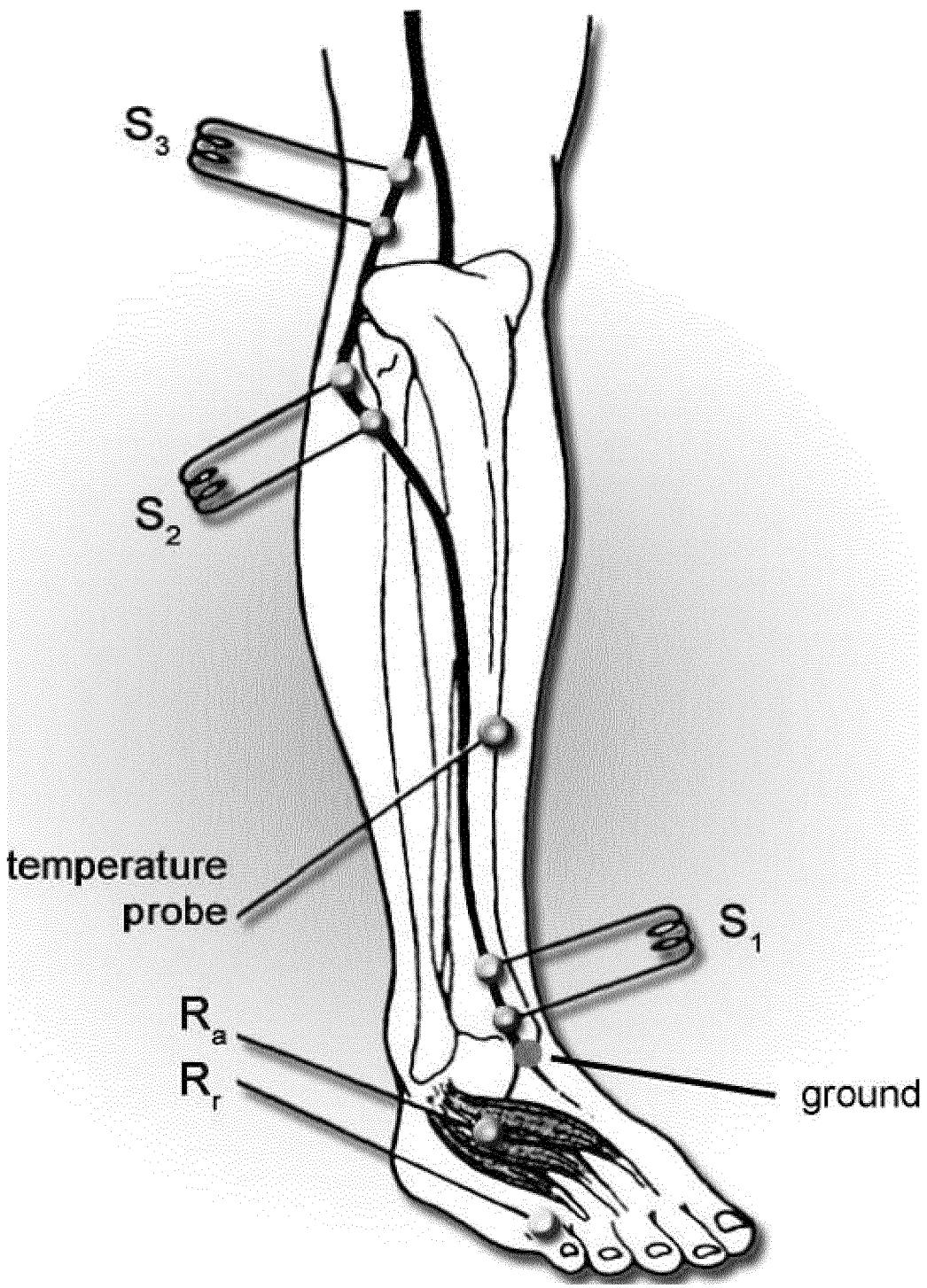
FIG. 7: Peroneal Nerve Conduction Study. Placement of recording and stimulating electrodes. Ra=recording active electrode. Rr=recording reference electrode. Recording site: EDB Distal distance: 90 mm. Stimulating sites: S1: Ankle.

Set the filters for motor nerve conduction study. The sweep speed may be set at 3-5 ms/div (increase if necessary), and the gain may be set at 0.5-5 mV/div. Locate, lightly abrade and clean the skin at the recording and stimulating sites. Place the active recording electrode over the end-plate region of the extensor digitorum brevis muscle (EDB) (FIG. 7).

Place the reference electrode at the base of the fifth toe. Place the ground electrode between the recording and stimulating electrodes. Record the temperature in the lower leg. Temperature should be >31° C.

S1 Ankle: Place the stimulating cathode over the peroneal nerve at the ankle, 80-100 mm, preferably 90 mm proximal to the recording electrode on the anterior surface of the ankle, slightly lateral to the tibialis anterior tendon. Stimulate the nerve at the ankle to achieve a supramaximal response (M wave from the ankle).

S2 Below fibular head: Place the stimulating cathode over the peroneal nerve just below the head of the fibula. Stimulate the nerve below the fibular head to achieve a supramaximal response (M wave from below fibular head).

S3 Lateral popliteal fossa: Place the stimulating cathode over the Peroneal nerve in the lateral popliteal fossa, at least 80 mm to the below fibular head, just medial to the tendon of the long head of the biceps femoris muscle. Stimulate the nerve just inside to achieve a supramaximal response (M wave from the lateral popliteal fossa).

Place and check the cursors for amplitude (baseline-negative peak) at a sensitivity, which shows the entire response, spread over 2 or 3 divisions (usually 2-5 mV/div). Increase the gain to 0.5 mV/div, place and check the cursors for latency at the onset of the clipped peak of each M wave.

Measure and record the distances (ankle to EDB electrode, below fibular head to ankle and lateral popliteal fossa to below fibular head) to the nearest 1 mm. Measure and record the temperature in the lower leg.

If the muscle action potential amplitude is greater with supramaximal stimulation at the knee than at the ankle—and the stimulating and recording electrodes have been correctly placed—then the presence of an accessory peroneal nerve branch should be suspected.

To check for this possibility, record the EDB and stimulate at the ankle, behind the lateral malleolus; this allows recording of the response from accessory peroneal branch.

5. Technical Concerns

The nerve conduction studies are particularly difficult to perform in subjects with CIDP since the responses may be low amplitude, dispersed and difficult to obtain. The changes expected are a combination of disproportionate prolonged distal latencies, marked slowing of conduction velocities, delayed or absent F responses and conduction block/abnormal temporal dispersion. Artifacts and technical errors are common and failure to recognize these factors may result in a multitude of technical errors that can interfere with the accuracy of the results. Attention to the following details may help to minimize errors and variance.

5.1 Temperature

Reduced temperature has a marked effect upon motor responses, such as increasing amplitudes and latencies and decreasing conduction velocities.

It is important to warm the limbs properly at the beginning of each NCS and maintain the correct temperature required as per protocol during the test, since temperature decreases rapidly in the lower extremities due to lower ambient temperature. Temperature should be recorded several minutes after warming to allow stabilization. Radiant lamp should be used at low setting to allow gradual and deep warming of the limb. Large differences of several degrees between start and end temperatures should be avoided. The ambient room temperature should also be controlled appropriately.

5.2 Stimulation

The stimulation intensity used for all motor responses must be supramaximal. However, in chronic demyelinating neuropathy, the electrical activation may be abnormally increased. Stimulation intensity has to be adjusted along with duration to reduce shock artifact as much as possible.

5.3 Distance Measurements

Distance measurement is a common source of error and should be checked carefully. Accurate measurement of distances will provide reliable and reproducible nerve conduction results.

The distal distance should be 70 mm for median motor, 65 mm for ulnar motor, and 90 mm for peroneal motor nerve studies since an increased distance between recording and stimulating electrodes may cause an increase in latency and decrease in amplitude.

For the peroneal motor nerve studies, distance between below fibular head and lateral popliteal fossa should be at least 80 mm.

For motor nerve conduction, the active recording electrode should be placed on the muscle belly and the reference electrode on an electrically silent, distal point. Different placements of the reference electrode may cause a reduction in amplitude and change in the morphology of the response.

5.4 Machine Settings

Amplifier and filters settings have an effect on the nerve conduction data and should be used as per protocol and maintained during the entire study. It is important to use the same gain and sweep speed settings at different stimulation sites along the same nerve tested in order to determine accurate latency and amplitude measurements. It is also recommended to use the same sweep speed settings for latencies measurements at subsequent visits for the same subject. If the filter settings are changed, the latency, amplitude, and configuration of the waveform will also change.

Use of incorrect filters will yield unreliable nerve conduction data; hence, if the EMG machine does not allow for preset filters, ensure that the appropriate filter settings as per protocol are used prior to beginning the nerve testing. Latency values will decrease as increased amplification provides an earlier deviation from the apparent baseline. Motor response latencies should be taken at the onset of the clipped M wave (using a gain setting of 0.5 mV/div). For very low motor amplitude responses, latency is measured at the onset of the M wave displayed over at least two divisions.

Design/Methods:

The study was a randomised, double-blind study investigating 0.2 g/kg (low) and 0.4 g/kg (high) weekly doses of maintenance SCIG IgPro20 (Hizentra, CSL Behring) versus placebo (N=172). After Ig dependency testing, and IVIG restabilisation, patients were randomised to SCIG or placebo for 25 weeks or until early termination.

Nerve conduction studies (NCS) were performed before study drug administration. Relapse rate (defined as a 1 point decrease by adjusted Inflammatory Neuropathy Cause and Treatment score) comparisons were undertaken on patients with assumed non-axonal damage versus assumed axonal damage based on a cut-off amplitude at the distal stimulation site: >1 mV for the foot.

In particular, standard nerve conduction studies of the peroneal motor nerves were performed on all subjects using the Counterpoint instrument (Medtronic, Mississauga, Canada). Recordings were performed with temperature control (32-34° C.), careful distance measurements (90 mm for the peroneal motor nerve), and recording of well-defined and artifact-free responses. Surface silver/silver chloride discs with a standardized size of 4×7 mm were used to record all nerve responses. Three nerve conduction studies were done within 2-3 weeks. Latencies and amplitudes were determined automatically, distance values were entered into the Counterpoint, and conduction velocities were calculated automatically.

Results:

Patients with assumed non-axonal damage who received placebo had a 73% relapse rate versus 39% on low-dose and 19% on high-dose SCIG. Patients with assumed axonal damage had relapse rates of 25% 30% and 19% for placebo, low-dose and high-dose SCIG, respectively (Table below).

findings could help in redesigning future trials including maintenance regimens based on NCS categorisation of patients.

The invention claimed is:

1. A method for treating chronic inflammatory demyelinating polyneuropathy (CIDP), comprising administering an effective amount of an immunoglobulin G product to a CIDP patient who has been diagnosed as having non-axonal damage or mild axonal damage by an electrophysiology measurement of a compound muscle action potential in the CIDP patient, wherein the compound muscle action potential in the CIDP patient is
   (1) higher than 1 mV at the foot,
   (2) higher than 2 mV at the wrist, and/or
   (3) at least 50% of the mean compound muscle action potential measured in a healthy subject.

2. The method of claim 1, wherein the electrophysiology measurements are carried out at the ulnar motor nerve, at the median motor nerve, using a stimulation electrode and a recording electrode.

3. The method of claim 2, wherein the electrophysiology measurements are carried out at the wrist at the ulnar motor nerve, at the wrist at the median motor nerve, and/or at the foot at the peroneal motor nerve.

4. The method of claim 2, wherein the distance between the stimulation electrode and the recording electrode is:
   (i) between 55 and 75 mm for the ulnar motor nerve,
   (ii) between 60 and 80 mm for the median motor nerve, and/or
   (iii) between 80 and 100 mm for the peroneal motor nerve.

5. The method of claim 2, wherein the distance between the stimulation electrode and the recording electrode is 65 mm for the ulnar motor nerve, 70 mm for the median motor nerve, and/or 90 mm for the peroneal motor nerve.

6. The method of claim 1, wherein the electrophysiology measurement is carried out at a temperature between 30-36° C.

7. The method of claim 1, wherein the non-axonal damage has been determined by nerve biopsy.

| | Relapse Number of patients % (95% Wilson CI) | | | Difference % (95% Wilson CI) | | |
|---|---|---|---|---|---|---|
| | Placebo (N = 57) | Low-dose SCIG (N = 53) | High-dose SCIG (N = 57) | Low-dose vs placebo | High-dose vs placebo | High-dose vs low-dose |
| Assumed non-axonal damage N = 86 | 27 of 37 patients 72.97% (57.02% to 84.6%) | 9 of 23 patients 39.13% (22.16% to 59.21%) | 5 of 26 patients 19.23% (8.51% to 37.88%) | −33.84% (−51.72% to −12.27%) S | −53.74% (−67.66% to −33.46%) S | 19.9% (−39.41% to 1.37%) NS |
| Assumed axonal damage N = 81 | 5 of 20 patients 25.0% (11.19% to 46.87%) | 9 of 30 patients 30.0% (16.66% to 36.28%) | 6 of 31 patients 19.4% (9.19% to 36.28%) | 5% (−16.62% to 24.33%) | 5.6% (−25.97% to 12.91%) | 10.65% (−28.09% to 7.49%) |

CONCLUSIONS

CIDP patients with assumed non-axonal damage had a high relapse rate when switched from IVIG to placebo that was significantly reduced in patients switched to SCIG therapy. Relapse rates were lower in assumed axonal damage patients and were not influenced by SCIG. These 8. The method of claim 1, wherein the immunoglobulin product is administered at a dose of 0.1-0.4 g/kg patient weight per 5-10 days.

9. The method of claim 8, wherein the immunoglobulin product is administered subcutaneously at a dose of 0.4 g/kg patient weight per week.

10. The method of claim 1, wherein the CIPD relapse rate is reduced by more than 30% when compared to placebo.

\* \* \* \* \*

UNITED STATES PATENT AND TRADEMARK OFFICE
CERTIFICATE OF CORRECTION

| | |
|---|---|
| PATENT NO. | : 12,325,738 B2 |
| APPLICATION NO. | : 17/056632 |
| DATED | : June 10, 2025 |
| INVENTOR(S) | : Vera Bril et al. |

Page 1 of 1

It is certified that error appears in the above-identified patent and that said Letters Patent is hereby corrected as shown below:

In the Claims

Claim 2, Column 20, Lines 21-22, "using a simulation electrode and a recording electrode" should read as —and/or at the peroneal motor nerve using a simulation electrode and a recording electrode—.

Claim 10, Column 21, Line 1, "CIPD" should read as —CIDP—.

Signed and Sealed this
Twelfth Day of August, 2025

Coke Morgan Stewart
*Acting Director of the United States Patent and Trademark Office*